(12) United States Patent
Yeh et al.

(10) Patent No.: US 6,307,053 B1
(45) Date of Patent: Oct. 23, 2001

(54) PROCESS FOR PREPARING IMIDACLOPRID

(75) Inventors: Chun-Lin Yeh; Chien-Hsing Chen, both of Taichung (TW)

(73) Assignee: Sinon Corporation, Taichung (TW)

( * ) Notice: Subject to any disclaimer, the term of this patent is extended or adjusted under 35 U.S.C. 154(b) by 0 days.

(21) Appl. No.: 09/752,416

(22) Filed: Dec. 29, 2000

(51) Int. Cl.[7] .................................................. C07D 401/06
(52) U.S. Cl. ............................................................ 546/274.7
(58) Field of Search ........................................... 546/274.7

(56) References Cited

U.S. PATENT DOCUMENTS 5,310,920 * 5/1994 Kodaka et al. ...................... 514/341

* cited by examiner

*Primary Examiner*—Patricia L. Morris
(74) *Attorney, Agent, or Firm*—Brinks Hofer Gilson & Lione

(57) ABSTRACT

A process for preparing imidacloprid involves reacting 2-nitroiminoimidazolidine with 2-chloro-5-chloromethyl pyridine in the presence of an alkali carbonate in an organic solvent. A stoichiometric amount of the 2-chloro-5-chloromethyl pyridine is gradually added into mixture of a corresponding stoichiometric amount of the 2-nitroiminoimidazolidine and the organic solvent under reflux condition.

7 Claims, No Drawings

PROCESS FOR PREPARING IMIDACLOPRID

BACKGROUND OF THE INVENTION

1. Field of the Invention

This invention relates to a process for preparing imidacloprid in the presence of an alkali carbonate in an organic solvent.

2. Description of the Related Art

Imidacloprid (1-[(6-Chloro-3-pyridinyl) methyl]-4,5-dihydro-N-nitro-1H-imidazol-2-amine) is known as an insecticide, and is a neonicotinoid compound, which has been disclosed in U.S. Pat. No. 4,742,060, and which has a formula as shown below:

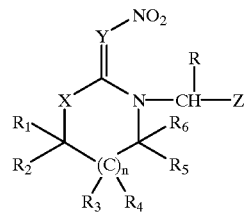

Wherein n=0 or 1; X=S, O, —N—R7 or —CH—R8; Y=N or =C—R9; R7, R8, R9=hydrogen or specifical organic radicals; Z=5- or 6-membered nitrogen-containing heterocyclic ring; R1, R2, R5, R6=hydrogen or alkyl group; R3, R4=hydrogen, hydroxy group or alkyl group. The neonicotinoid compound can be synthesized by reacting a hetercyclic compound with an amine compound in the presence of an alkali base in an organic solvent.

The aforesaid alkali base can be NaH or an alkali carbonate when the amine compound employed in the reaction is a uni-amine compound. However, it is preferable to employ NaH when the amine compound employed in the reaction is a di-amine compound. The alkali carbonate is not suitable for the reaction involving the di-amine compound due to a relatively poor yield. The aforementioned reactions can be represented by the following two examples:

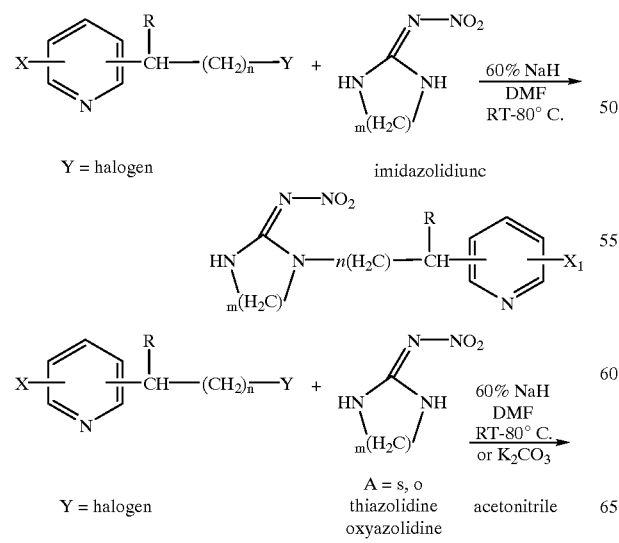

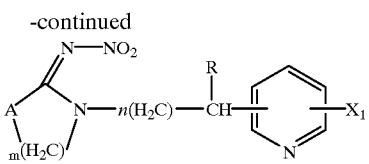

Imidacloprid can be prepared by reacting 2-nitroiminoimidazolidine (a di-amine compound) with 2-chloro-5-chloromethyl pyridine (CCMP) in the presence of 60% NaH in an organic solvent, such as DMF (diemthyl formamide), at a temperature ranging from room temperature to about 80° C. However, the use of NaH would give rise to safety concerns and transport problems. Moreover, the reaction has a poor yield. It is found that when NaH is replaced by alkali carbonate in the aforementioned reaction, a relatively large amount of by product is produced. The reaction can be represented as follows:

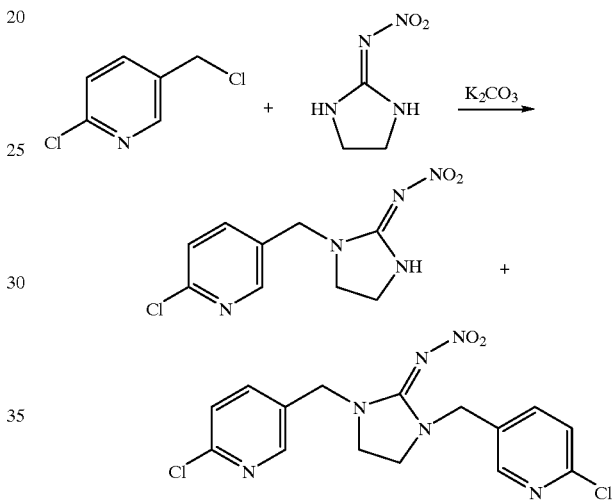

Due to the aforementioned drawbacks, a two-step reaction process for preparing Imidacloprid has been proposed heretofore, which can be represented as follows:

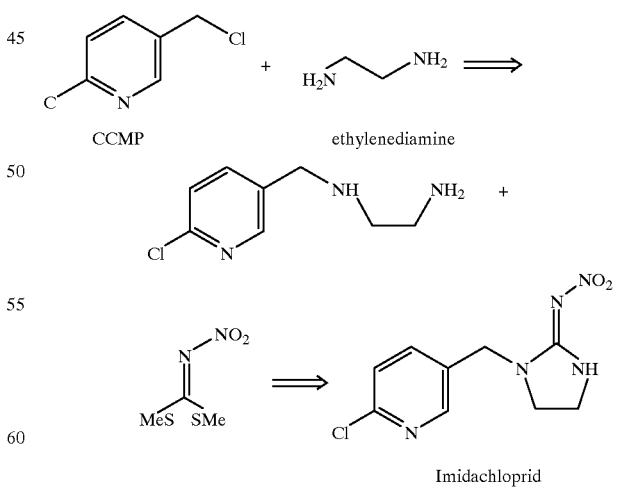

While the aforesaid yield can be improved and the aforesaid safety concerns and transport problems can be overcome by using the two-step reaction, the two-step reaction process is complex and costly.

SUMMARY OF THE INVENTION

Therefore, it is an object of the present invention to provide a process for preparing imidacloprid that is capable of overcoming the aforesaid drawbacks and that significantly improves the yield of the aforesaid reaction.

Accordingly, a process for preparing imidacloprid according to the present invention, comprises reacting 2-nitroiminoimidazolidine with 2-chloro-5-chloromethyl pyridine in the presence of an alkali carbonate in an organic solvent, wherein a stoichiometric amount of the 2-chloro-5-chloromethyl pyridine is gradually added into mixture of a corresponding stoichiometric amount of the 2-nitroiminoimidazolidine and the organic solvent under reflux condition.

DETAILED DESCRIPTION OF THE PREFERRED EMBODIMENT

Preparation of imidacloprid according to the process of this invention is described in detail as follows.

The process for preparing imidacloprid comprises reacting 2-nitroiminoimidazolidine with 2-chloro-5-chloromethyl pyridine in the presence of an alkali carbonate in an organic solvent, wherein a stoichiometric amount of the 2-chloro-5-chloromethyl pyridine is gradually added into mixture of a corresponding stoichiometric amount of the 2-nitroiminoimidazolidine and the organic solvent under reflux condition.

Preferably, the stoichiometric amount of the 2-chloro-5-chloromethyl pyridine is dropwisely and continuously added into the mixture of the corresponding stoichiometric amount of the 2-nitroiminoimidazolidine and the organic solvent, and more preferably, the stoichiometric amount of the 2-chloro-5-chloromethyl pyridine is gradually and continuously added into the mixture of the corresponding stoichiometric amount of the 2-nitroiminoimidazolidine and the organic solvent at a rate of less than 0.03 equivalent of the 2-chloro-5-chloromethyl pyridine per minute.

Preferably, the alkali carbonate contains an alkali element that is selected from a group consisting of lithium, sodium, and potassium, and more preferably contains potassium.

Preferably, the organic solvent is selected from a group consisting of alcohols, ketones, DMF, and acetonitrile, and is more preferably acetonitrile.

The following Examples and Comparative Example illustrate the unexpectedly better results of this invention over the aforesaid prior art.

EXAMPLE 1

7.8 g (60 mmol) of 2-nitroiminoimidazolidine and 12.1 g (87.5 mmol) of potassium carbonate were dissolved in 60 ml of acetonitrile in a reflux flask. The mixture is heated to a temperature sufficient for achieving reflux operating condition. 8.1 g (50.0 mole) of 2-chloro-5-chloromethyl pyridine is dissolved in 40 ml of acetonitrile, and is dropwisely and continuously added into the flask under the reflux condition for a period of 0.5 hr, i.e. the addition rate is about 1.5 ml/minute (the addition rate at the onset of the reaction corresponds to 0.0278 equivalent of 2-chloro-5-chloromethyl pyridine per equivalent of 2-nitroiminoimidazolidine per minute) After completion of the reaction, the mixture is subjected to filtration. The filtrate is concentrated, and is further purified. The yield and the value of A.I. (Active Ingredient) determined by liquid chromatography for this Example is listed in Table 1.

TABLE 1

| | Period of addition of 2-chloro-5-chloromethyl pyridine (hr) | Imidacloprid (crude) | |
|---|---|---|---|
| | | Yield (%) | AI (%) |
| Comparative Example 1 | 0.0 | 83.90 | 80.53 |
| Example 1 | 0.5 | 84.30 | 82.60 |
| Example 2 | 1.0 | 87.50 | 85.70 |
| Example 3 | 2.0 | 89.18 | 87.67 |
| Example 4 | 4.0 | 91.24 | 89.70 |
| Example 5 | 5.0 | 92.16 | 90.60 |
| Example 6 | 6.5 | 92.30 | 90.85 |

EXAMPLES 2 TO 6

Example 1 was repeated, except that the periods for addition of the 2-chloro-5-chloromethyl pyridine into the flask for Examples 2 to 6 are respectively 1 hr, 2 hrs, 4 hrs, 5 hrs, and 6.5 hrs. The yields and the values of A.I. for Examples 2 to 6 are listed in Table 1.

COMPARATIVE EXAMPLE 1

Example 1 was repeated, except that the period for addition of the 2-chloro-5-chloromethyl pyridine into the flask is substantially zero, i.e. the entire amount of the 2-chloro-5-chloromethyl pyridine was added into the flask at the same time. The yield and the value of the A.I. for this Comparative Example are listed in Table 1.

Results of Examples 1 to 6 and the Comparative Example 1 show that yield of imidacloprid increases as the addition rate of 2-chloro-5-chloromethyl pyridine decreases.

EXAMPLES 7 TO 9

Examples 7 to 9 investigated effect of equivalent of 2-nitroiminoimidazolidine on the yield of imidacloprid. Experimental procedures for Examples 7 to 9 are similar to those of Example 1. Amounts of 2-chloro-5-chloromethyl pyridine and potassium carbonate employed in Examples 7 to 9 are respectively 1 equivalent and 1.5 equivalents, and the organic solvent employed in Examples 7 to 9 is 2-butanone. The yields and the values of A. I. are listed in Table 2.

TABLE 2

| | Equivalent of 2-nitroiminoimidazolidine | imidacloprid (purified) | |
|---|---|---|---|
| | | Yield (%) | AI (%) |
| Example 7 | 1.0 | 58 | 99 |
| Example 8 | 1.1 | 63 | 99 |
| Example 9 | 1.2 | 66 | 99 |

Results of Examples 7 to 9 show that the yield of imidacloprid increases as the ratio of the equivalent of 2-nitroiminoimidazolidine to the equivalent of imidacloprid increases from 1 to 1.2.

EXAMPLES 10 TO 13

Examples 10 to 13 investigated effect of equivalent of potassium carbonate on the yield of imidacloprid. Experimental procedures for Examples 10 to 12 are similar to those of Example 1. Amounts of 2-chloro-5-chloromethyl pyridine and 2-nitroiminoimidazolidine employed in Examples 10 to 13 are respectively 1 equivalent and 1.2 equivalents, and the organic solvent employed in Examples 10 to 13 is 2-butanone. The yields and the values of A.I. are listed in Table 3.

TABLE 3

|  | Equivalent of potassium carbonate | imidacloprid (purified) | |
| --- | --- | --- | --- |
|  |  | Yield (%) | AI (%) |
| Example 10 | 1.00 | 51 | 99 |
| Example 11 | 1.25 | 58 | 99 |
| Example 12 | 1.50 | 67 | 99 |
| Example 13 | 1.75 | 66 | 99 |

Results of Examples 10 to 13 show that the yield of imidacloprid increases as the ratio of the equivalent of potassium carbonate to the equivalent of imidacloprid increases from 1 to 1.75.

EXAMPLES 14 TO 17

Examples 14 to 17 investigated effect of the organic solvent on the yield of imidacloprid. Experimental procedures for Examples 14 to 17 are similar to those of Example 1. Amounts of 2-chloro-5-chloromethyl pyridine, 2-nitroiminoimidazolidine, and potassium carbonate employed in Examples 14 to 17 are respectively 1 equivalent, 1.2 equivalents, and 1.5 equivalents, and the organic solvents employed in the reactions are respectively DMF, isopropanol, acetone, and acetonitrile. The yields and the values of A.I. are listed in Table 4.

TABLE 4

|  |  | Imidacloprid (purified) | |
| --- | --- | --- | --- |
|  | Organic solvent employed | Yield (%) | AI (%) |
| Example 14 | DMF | 49 | 98 |
| Example 15 | Isopropanol | 50 | 98 |
| Example 16 | Acetone | 61 | 99 |
| Example 17 | acetonitrile | 75 | 99 |

Results of Examples 14 to 17 show that acetonitrile has the highest yield of imidacloprid among the organic solvents employed in the aforesaid Examples.

With the invention thus explained, it is apparent that various modifications and variations can be made without departing from the spirit of the present invention. It is therefore intended that the invention be limited only as recited in the appended claims.

We claim:

1. A process for preparing imidacloprid, comprising:

reacting 2-nitroiminoimidazolidine with 2-chloro-5-chloromethyl pyridine in the presence of an alkali carbonate in an organic solvent, wherein a stoichiometric amount of the 2-chloro-5-chloromethyl pyridine is gradually added into mixture of a corresponding stoichiometric amount of the 2-nitroiminoimidazolidine and the organic solvent under reflux condition.

2. The process of claim 1, wherein the stoichiometric amount of the 2-chloro-5-chloromethyl pyridine is dropwisely and continuously added into the mixture of the corresponding stoichiometric amount of the 2-nitroiminoimidazolidine and the organic solvent.

3. The process of claim 1, wherein the stoichiometric amount of the 2-chloro-5-chloromethyl pyridine is gradually and continuously added into the mixture of the corresponding stoichiometric amount of the 2-nitroiminoimidazolidine and the organic solvent at a rate of less than 0.03 equivalent of the 2-chloro-5-chloromethyl pyridine per minute.

4. The process of claim 1, wherein the alkali carbonate contains an alkali element that is selected from a group consisting of lithium, sodium, and potassium.

5. The process of claim 4, wherein the alkali carbonate is potassium carbonate.

6. The process of claim 1, wherein the organic solvent is selected from a group consisting of alcohols, ketones, DMF, and acetonitrile.

7. The process of claim 1, wherein the organic solvent is acetonitrile.

* * * * *